United States Patent [19]

Hamanaka

[11] Patent Number: 4,486,411

[45] Date of Patent: Dec. 4, 1984

[54] BETA-LACTAMASE INHIBITING 6-BETA-SULFONYLOXYPENICILLANIC ACID DERIVATIVES

[75] Inventor: Ernest S. Hamanaka, Groton, Conn.

[73] Assignee: Pfizer Inc., New York, N.Y.

[21] Appl. No.: 279,404

[22] Filed: Jul. 1, 1981

Related U.S. Application Data

[63] Continuation-in-part of Ser. No. 132,443, Mar. 21, 1980, abandoned.

[51] Int. Cl.$^3$ ............................................. A61K 35/00
[52] U.S. Cl. .................................................... 424/114
[58] Field of Search ........................................ 424/114

[56] References Cited

U.S. PATENT DOCUMENTS 4,143,046  3/1979  Sheehan et al. .................... 424/270

FOREIGN PATENT DOCUMENTS 2416492 10/1974 Fed. Rep. of Germany ...... 424/270
2052981  2/1981 United Kingdom .

OTHER PUBLICATIONS

PDR, 27 Ed., 1973, pp. 1049–1051.
Brown et al., J. Antibiotics, 29, pp. 668–669, (1976).
English et al., Antimicrob Agents and Chemotherap. 14, pp. 414–419, (1978).
Lo et al., J. Am. Chem. Soc., 94, p. 8253, (1972).

*Primary Examiner*—Jerome D. Goldberg
*Attorney, Agent, or Firm*—Charles J. Knuth; Albert E. Frost; Robert K. Blackwood

[57] ABSTRACT

6-Beta-sulfonyloxypenicillanic acid derivatives are novel beta-lactamase inhibitors, useful in combination with standard beta-lactam antibiotics against bacterial strains otherwise resistant to said beta-lactam antibiotics by dint of their production of beta-lactamases.

26 Claims, No Drawings

BETA-LACTAMASE INHIBITING 6-BETA-SULFONYLOXYPENICILLANIC ACID DERIVATIVES

CROSS REFERENCE TO RELATED APPLICATIONS

This application is a continuation-in-part of copending application Ser. No. 132,443, filed Mar. 21, 1980 now abandoned.

BACKGROUND OF THE INVENTION

One of the most well-known and widely-used class of antibacterial agents is the beta-lactam antibiotics. These compounds are characterized by a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (pencillin G), phenoxymethylpenicillin (penicillin V), ampicillin and carbenicillin; typical examples of common cephalosporins are cephalothin, cephalexin and cefazolin.

However, despite the wide use and acceptance of the beta-lactam antibiotics as valuable chemotherapeutic agents, they suffer from the major drawback that certain members are not active against certain microorganisms. In many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components. A variety of compounds have been reported to possess beta-lactamase inhibitory activity, including clavulanic acid and other fermentation-derived compounds [Brown et al., J. Antibiot. 29, 668 (1976)]as well as compounds derived from beta-lactam antibiotics by partial synthesis [see for example English et al., Antimicrobial Agents and Chemotherapy 14, 414 (1978)].

6-Beta-hydroxypenicillanic acid (employed as starting material in the present synthesis), its benzyl ester, as well as various acylated derivatives thereof, including phenoxyacetyl, phenylacetyl, benzenesulfonyl and methanesulfonyl, have been previously disclosed [Sheehan and Lo, U.S. Pat. No, 4,143,046; see also Lo and Sheehan, J. Am. Chem. Soc. 94, 8253 (1972)]. Sheehan and Lo do not report these compounds to possess activity as beta-lactamase inhibitors.

SUMMARY OF THE INVENTION

According to the present invention there are provided certain chemical compounds novelly possessing activity as inhibitors of beta-lactamases. By this mechanism, these compounds enhance the activity of beta-lactam antibiotics (penicillins and cephalosporins), in particular against Proteus infections, when administered to mammals either orally or by a parenteral route (intramuscular, intravenous, intraperitoneal).

These pharmaceutically useful compounds are 6-beta-sulfonyloxypenicillanic acid derivatives of the following structure:

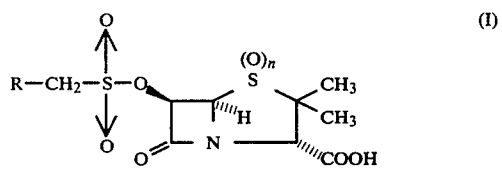

together with pharmaceutically acceptable salts and esters hydrolyzed under physiological conditions, wherein R is hydrogen, $(C_1-C_3)$alkyl, or phenyl, and n is a integer of value 0 to 2. Among these, the preferred compounds have R either as hydrogen or as phenyl and n as zero.

Exemplary of the beta-lactam antibiotics whose activity is enhanced by these compounds are amoxicillin, ampicillin, carbenicillin, cefazolin, cefoperazone, cephalexin, cefachlor, cephaloridine, cephalothin, cephradine, penicillin G and penicillin V in their various forms (salts, solvates, etc.). Although the compounds of the present invention can be administered separately from the beta-lactam antibiotic, combination dosage forms are preferred. When used parenterally, the compounds of this invention are conveniently combined with beta-lactam antibiotics which find parenteral use, e.g., ampicillin trihydrate, ampicillin sodium, carbenicillin disodium, cefazolin sodium, cefoperazone sodium, cephaloridine, penicillin G potassium, penicillin G sodium and penicillin G procaine. For oral administration they are combined with beta-lactam antibiotics such as amoxicillin, ampicillin, cephalexin, cefachlor and cephradine. Certain prodrug esters of the compounds of the present invention (e.g. pivaloyloxymethyl, 1-ethoxycarbonyloxyethyl and 1,3-dihydro-3-oxobenzo[c]furan-1-yl) which are well absorbed and readily hydrolyzed under physiological conditions, are particularly useful for combination with oral beta-lactam antibiotics.

DETAILS OF THE INVENTION

The 6-beta-sulfonyloxypenicillanic acid derivatives employed in the present invention are readily prepared, employing the following chemistry:

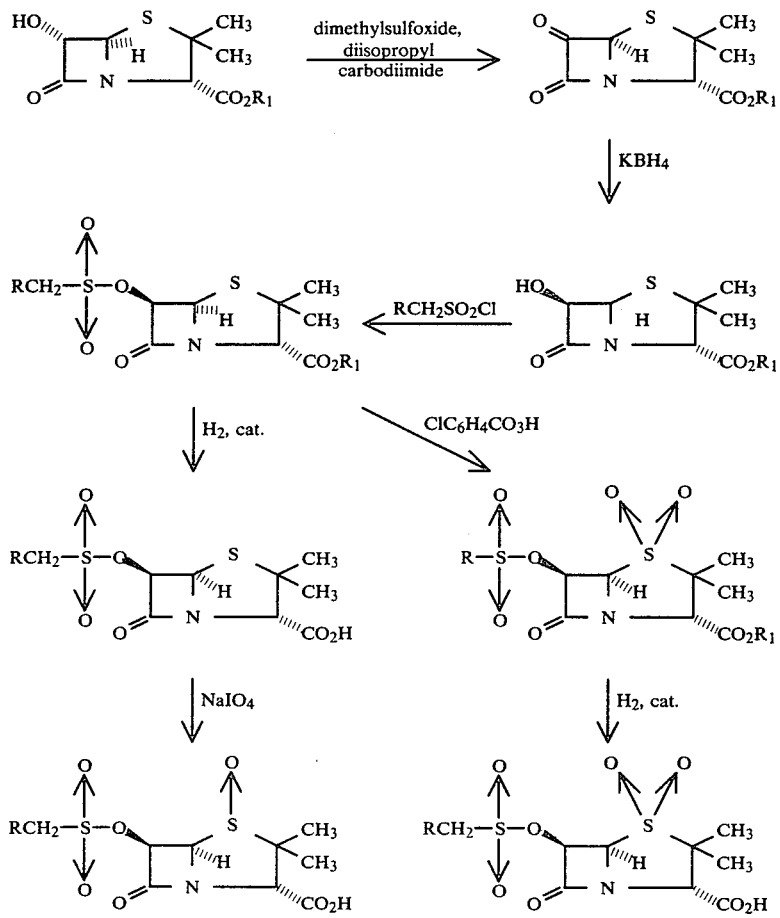

wherein R has the same meaning as heretofor noted and R[1] is benzyl, p-nitrobenzyl or other protective group removable by hydrogenolysis.

6-Alpha-hydroxypenicillanic esters are prepared by the method of Hauser and Sigg [Helv. Chim. Acta. 50, 1327 (1967)] and converted to the requisite 6-beta-hydroxypenicillanic esters according to Lo and Sheehan [J. Am. Chem. Soc. 94, 8253 (1972)].

Sulfonation of 6-beta-hydroxypenicillanic derivatives can be carried out before or after removal of the benzyl type protecting group. In either case, sulfonation is accomplished by reacting the alcohol with a sulfonyl halide in an inert solvent, i.e. a solvent in which both the alcohol and the acid chloride have solubility sufficient to lead to the desired reaction, but which do not react to any significant degree with either reactants or product. Suitable solvents for this purpose include, but are not restricted to, methylene chloride, chloroform, dimethoxyethane, tetrahydrofuran and dimethylformamide. The reaction can be carried out under a wide temperature range (e.g. $-10°$ to $80°$ C.), high enough that the reaction proceeds at a reasonable rate, but low enough to preclude undue thermal decomposition of products or reactants. Beta-lactams being somewhat labile, lower temperatures are preferred, the range $20°-25°$ C. being quite satisfactory. The reaction is usually carried out in the presence of one equivalent of tertiary amine base, which catalyzes the reaction, and neutralizes the hydrogen chloride produced as a by-product of the reaction. Suitable bases are triethylamine, N-methyl-morpholine, N-methylpyrrolidine, N-methylpiperidine, quinuclidine, and dimethylaniline.

When the sulfone (1,1-dioxide) is desired, oxidation can be carried out at any stage in the synthesis, including before or after the acylation step or before or after removal of the benzyl protecting group. Oxidation is usually carried out after acylation, but before removal of the protective group, and is conveniently carried out using a peroxycarboxylic acid (e.g. m-chloroperbenzoic acid) in an inert solvent such as methylene chloride or chloroform. By inert solvent is meant one which will dissolve sufficient reactants to lead to the desired reaction, but which does not react to any significant degree with either reactants or product. Suitable solvents for this purpose include, but are not restricted to methylene chloride, chloroform, benzene or toluene. The temperature can be over a wide range (e.g. $-10°$ to $80°$ C.), high enough that the reaction proceeds at a reasonable rate, but low enough to avoid undue decomposition of reactants or product. Beta-lactams being somewhat labile, lower temperatures in the range are preferred, ambient temperatures of $20°-25°$ C. being quite satisfactory.

Hydrogenolysis of the benzyl type protective group can be carried out before or after sulfonation, as well as before or after oxidation to sulfone or sulfoxide. In any case, the reaction is conveniently carried out over a noble metal catalyst (conveniently prereduced 5% palladium on calcium carbonate), generally at a near neutral pH (e.g. pH 5.5), which is maintained on the acid side by the carboxylic acid produced in the reaction, in the presence of a hydroxylic solvent. Suitable solvents include, but are not limited to, aqueous tetrahydrofuran, aqueous dimethoxyethane, methanolic tetrahydrofuran, isopropanol, or aqueous ethanol. Temperature is not critical and can be over a wide range (e.g. −10° C. to 80° C.). Temperatures lower in the range minimize degradation of the beta-lactam starting material and product. Optimal balance of these factors is a matter of straightforward experimentation by those skilled in the art.

The sulfoxides of this invention can be prepared by oxidation of 6-beta-hydroxypenicillanic acid derivatives with sodium metaperiodate (1 equivalent) in aqueous media. The oxidation can be carried out after sulfonation and removal of the benzyl ester group, for example by oxidizing the sodium salt of the 6-beta-sulfonyloxypenicillanic acid in aqueous media at ambient temperatures.

The prodrug esters of the compounds of the present invention are prepared by standard procedures found in the literature. For example, the acids of the present invention, in the presence of triethylamine and potassium bicarbonate are reacted with chloromethylpivalate, bromomethyl acetate, 1,3-dihydro-3-oxobenzo[c]furan-1-yl bromide, 1-ethoxycarbonyloxyethyl chloride, respectively, to yield the corresponding pivaloyloxymethyl, acetoxymethyl,. 1,3-dihydro-3-oxobenzo[c]furan-1-yl and 1-ethoxycarbonyloxyethyl esters.

The pharmaceutically acceptable salts encompassed by the present invention include, but are not limited to those formed with the following: sodium, potassium, calcium, procaine, ethylenediamine, diethanolamine and piperazine. The alkali metal salts are conveniently formed by titrating the acid in aqueous organic media (e.g. aqueous tetrahydrofuran) with an equivalent of the alkali metal hydroxide, followed by removal of solvent (vacuum stripping or freeze drying). The alkaline earth salts are formed by treating a solution of the acid with an organic solvent-soluble calcium salt (e.g. anhydrous calcium chloride, calcium malate, calcium salicylate), the solvent being one from which the calcium salt of the 6-beta-penicillanic precipitates. Amine salts, such as the procaine salt are conveniently prepared by mixing equivalent amounts of the acid and the amine, dissolved separately in alcohol, followed by stripping of solvent, or addition of a non-solvent, such as ether.

The in vitro activity of the compounds of the formula I can be demonstrated by measuring their minimum inhibitory concentrations (MIC's) in mcg./ml. against a variety of microorganisms. The procedure which is followed is the one recommended by the International Collaborative Study on Antibiotic Sensitivity Testing [Ericcson and Sherris, Acta. Pathologica et Microbiologia Scandinav, Supp. 217, Sections A and B: 64–68 (1971)], and employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye. The manner in which the said compounds of the formula I increase the effectiveness of a beta-lactam antibiotic can be appreciated by reference to experiments in which the MIC of a given antibiotic alone, and a compound of the formula I alone, are measured. These MIC's are then compared with the MIC values obtained with a combination of the given antibiotic and the compound of the formula I wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in 'Manual of Clinical Microbiology', edited by Lenette, Spaulding and Truant, 2nd Edition, 1974, American Society for Microbiology.

Results of experiments illustrating that compounds of the formula II enhance the effectiveness of various beta-lactam antibiotics are reported in Tables I and II. The consistent and generally pronounced synergy against *Proteus morgani* of the test compounds in conjunction with either ampicillin or cefazolin is noteworthy. It is obvious that the combination of compounds of the formula II with beta-lactam antibiotics will show synergistic activity against other bacterial strains, including some freshly isolated in the clinics. Determination of this activity is a matter of routine application of this type of testing.

The compounds of the present invention are also evaluated in vitro by their ability to inhibit the hydrolysis of certain beta-lactam antibiotics by beta-lactamase enzymes. The hydrolysis of ampicillin and penicillin G was determined by the microiodometric method of Novick [Biochem. J. 83, 236 (1962)].

TABLE I

MIC Values of Sodium Methanesulfonyloxypenicillanate, Alone and in 1:1 Mixture with Beta-Lactam Antibiotics

| Microorganism | MIC Alone | MIC with Ampicillin | Response with Ampicillin | MIC with Cefazolin | Response with Cefazolin |
|---|---|---|---|---|---|
| *Staphylococcus aureus* 5 | 12.5 | ≦0.2 | No test | — | — |
| *Staphylococcus aureus* 400* | 6.25 | 3.12 | Additive | ≧0.2 | Synergy |
| *Escherichia coli* 266 | >200 | 3.12 | Antagonism | — | — |
| *Escherichia coli* 2* | >200 | 100 | Additive | 6.25 | No test |
| *Escherichia coli* 129* | >200 | >100 | No test | 50 | Antagonism |
| *Pseudomonas aeruginosa* | >200 | >100 | No test | >100 | No test |
| *Klebsiella* | >200 | 100 | Antagonism | 1.56 | No effect |

TABLE I-continued

MIC Values of Sodium Methanesulfonyloxypenicillanate,
Alone and in 1:1 Mixture with Beta-Lactam Antibiotics

| Microorganism | MIC Alone | MIC with Ampicillin | Response with Ampicillin | MIC with Cefazolin | Response with Cefazolin |
|---|---|---|---|---|---|
| pneumonia | | | | | |
| Proteus morgani | >200 | 1.56 | Pronounced synergy | 25 | Synergy |
| Serratia marcescens | >200 | 25 | Antagonism | 100 | Synergy |
| Enterobacter cloacae | >200 | 100 | Synergy | >100 | No test |

*Resistant variants

TABLE II

MIC Values of Sodium 6-Beta-(Alpha-Toluenesulfonyloxy)penicillanate,
Alone and 1:1 Mixture with Beta-Lactam Antibiotics
(Results of Two Separate Tests)

| Microorganism | MIC Alone | MIC with Ampicillin | Response with Ampicillin | MIC with Cefazolin | Response with Cefazolin |
|---|---|---|---|---|---|
| Staphylococcus aureus 5 | 6.25 | ≦0.2 | No test | — | — |
|  | 100 | ≦0.2 | No test | — | — |
| Staphylococcus aureus 400* | 6.25 | 3.12 | Additive | ≦0.2 | Synergy |
|  | 50 | 0.78 | Pronounced Synergy | 0.39 | Additive |
| Escherichia coli 266 | >200 | 3.12 | Antagonism | — | — |
|  | >200 | 1.56 | No effect | — | — |
| Escherichia coli 2* | >200 | >100 | No test | 12.5 | Antagonism |
|  | >200 | >100 | No test | 6.25 | No effect |
| Escherichia coli 129* | >200 | >100 | No test | 100 | Antagonism |
|  | >200 | >100 | No test | 50 | No effect |
| Pseudomonas aeruginosa | >200 | >100 | No test | >100 | No test |
|  | >200 | >100 | No test | >100 | No test |
| Klebsiella pneumonia | >200 | >100 | Antagonism | 0.78 | Additive |
|  | >200 | >100 | Antagonism | 0.78 | Additive |
| Proteus morgani | >200 | 3.12 | Pronounced synergy | 12.5 | Pronounced synergy |
|  | >200 | 3.12 | Pronounced synergy | 50 | Synergy |
| Serratia marcescens | >200 | 25 | Additive | >100 | No test |
|  | >200 | 100 | Antagonism | >100 | No test |
| Enterobacter cloacae | >200 | 100 | Synergy | 100 | Synergy |
|  | >200 | 100 | Synergy | 100 | Synergy |

*Resistant variants

Cephaloridine hydrolysis was measured by following the decrease in ultraviolet absorbance at 255 nm [O'Callaghan et al., Antimicrob. Agents Chemother. 1968, pp. 57–63 (1969)]. Conditions for both assays were idential: 0.5 M potassium phosphate, pH 6.5 and 37° C. Reactions were initiated by the addition of the cell-free beta-lactamase, except in the case of preincubation experiments in which the inhibitor and enzyme were incubated together in the assay mixture for 10 minutes before initiation of the reaction by addition of substrate. With the cell-free extracts of Staphylococcus aureus, Escherichia coli, Klebsiella pneumoniae and Pseudomonas aeruginosa, the substrate was ampicillin at 33 micro M (13 microg./ml.). Typical specific activities of the beta-lactamase preparations were, respectively, 6,019, 88,970, 260 and 76 micromol/hr. per mg. of protein. Penicillin G (33 micromol) was the substrate used with the Enterobacter cloacae beta-lactamase, which showed a typical specific activity of 10,080 micromol/hr. per mg. of protein.

Cell-free extracts were prepared by sonic treatment (using three 30-s bursts at 4° C. except for S. aureus, which was broken with a French press) of cultures grown in brain heart infusion on a rotary shaker incubator. For the S. aureus, P. aeruginosa, and E. cloacae strains, de novo synthesis of beta-lactamase was induced by growing a log-phase culture in the presence of a sublethal concentration of penicillin G at 100, 1,000, and 300 microg./ml, respectively, for 2.5 hr.

The beta-lactamase inhibiting activities of the compounds of this invention are summarized in Table III. Especially noteworthy is the activity of compounds of structures wherein R is hydrogen or phenyl and n is 0.

TABLE III

Activity of Compounds of the Structure II (Sodium Salts)
As Inhibitors of Cell Free Beta-Lactamases $$\text{RCH}_2\text{S}(=O)_2\text{-O-}[\beta\text{-lactam penicillanate}]\text{-COONa} \quad \text{II}$$

| Source of Beta-Lactamase | Antibiotic (conc.) | Inhibitor R | n | (conc.) | % Inhibition Beta-Lactam Hydrolysis |
|---|---|---|---|---|---|
| Staphylococcus aureus 01A400 | Ampicillin (33 μM) | H | 0 | 16.5 μM | 100 |
| | | | | 66 | 100 |
| | | C₆H₅ | 0 | 16.5 | 40.3, 78, 63.3 |
| | | | | 66 | 85, 91.4, 91, 87.2[a] |
| | | C₆H₅ | 2 | 66 | 36.2 |
| Escherichia coli 51A129 | Ampicillin (33 μM) | H | 0 | 66 | 4.4 |
| | | C₆H₅ | 0 | 16.5 | 14.0 |
| | | | | 66 | 15.8 |
| Klebsiella pneumoniae 53A129 | Ampicillin (33 μM) | H | 0 | 16.5 | 0 |
| | | C₆H₅ | 0 | 16.5 | 3.0 |
| | | | | 66 | 0 |
| Pseudomonas aeruginosa 52A104 | Cephaloridine (16.5 μM) | C₆H₅ | 0 | 16.5 | 92.6 |
| | Penicillin G (33 μM) | C₆H₅ | 0 | 66 | 100 |
| Enterobacter cloacae 67B009 | Penicillin G (33 μM) | H | 0 | 66 | 66.7 |
| | | C₆H₅ | 0 | 16.5 | 96, 100 |
| | | | | 66 | 96, 100 |
| | | C₆H₅ | 2 | 66 | 0 |
| | Cephaloridine (4 μM) | C₆H₅ | 0 | 16.5 | 100 |
| | Cephaloridine (33 μM) | C₆H₅ | 0 | 4 | 93.7 |
| | | | | 16.5 | 98.3 |
| | Cephalexin (33 μM) | C₆H₅ | 0 | 16.5 | 100 |

[a] Preincubation experiment

When employed in the form of the acid, or a pharmaceutically-acceptable salt, the preferred route of administration of the compounds of the present invention is the parenteral route. Therefore, when the beta-lactam antibiotic is administered orally, the sulfonyloxypenicillanic acid or salt is usually administered separately. However, when the beta-lactam antibiotic is dosed parenterally, the sulfonyloxypenicillanic acid can be administered separately, but is preferably co-administered in a combined dosage form—thus avoiding the inconvenience of multiple injections. The parenteral dosage forms which combine a beta-lactam antibiotic and a sulfonyloxypenicillanic acid of the present invention are typically prepared by suitable modification of dosage forms of the beta-lactam antibiotic which are already well-established clinically. The beta-lactamase inhibitor, usually in the form of a pharmaceutically-acceptable salt, is added in the desired proportion, generally a weight in the range of 0.5 to 2.0 times the weight of beta-lactam anbitiotic and preferably a weight substantially equal to that of the weight of the beta-lactam antibiotic. For example, the sodium salt of 6-beta-methanesulfonyloxy is formulated with buffered penicillin G sodium; the procaine salt is formulated with penicillin G procaine. Standard excipients, buffers, solvents, suspending agents, preservatives, etc. commonly used in conjunction with parenteral dosage forms of beta-lactam antibiotics are well-suited for use in the aforesaid combination dosage forms. Suspensions for intramuscular injection can be in preconstituted liquid form, or as dry powders for reconstitution shortly before injection. On the other hand, for reasons of stability, solutions for intramuscular or intravenous injection are generally formulated as a soluble, dry powder. Such dosage forms are usually reconstituted with sterile water for injection (U.S.P.) for intramuscular or intravenous use, while if administration is to be by slow intravenous infusion, reconstitution is usually with isotonic sodium chloride injection (U.S.P.) or dextrose injection (U.S.P.).

As mentioned above, when the compounds of the present invention are administered orally, it is preferred that they be in the form of a prodrug ester. When the beta-lactam antibiotic is administered orally, it is convenient to formulate the prodrug ester and the antibiotic together. Such combined oral dosage forms are typically prepared in the form of tablets or capsules by suitable modification of dosage forms of the beta-lactam antibiotic which are already established clinically. The beta-lactamase inhibitor, as the ester prodrug, is added in the desired proportion, generally a weight in the range of 0.5 to 2.0 times the weight of beta-lactam antibiotic, preferably a weight substantially equal to the weight of beta-lactam antibiotic, together with additional excipients, if desired.

The daily dosage of a sulfonyloxypenicillanic acid is in a range similar to that frequently used with beta-lactam antibiotics, e.g., 0.5 to 6 g. of the sulfonyl compound administered with 1 to 4 g. of beta-lactam antibiotic per day, usually in divided doses. It is preferred that the daily dose of sulfonyloxypenicillanic acid be substantially equal in weight to that of beta-lactam antibiotic.

The present invention is illustrated by the following examples. However, it should be understood that the invention is not limited to the specific details of these examples.

EXAMPLE 1 p-Nitrobenzyl 6-beta-(alpha-Toluenesulfonyloxy)penicillanate p-Nitrobenzyl 6-beta-hydroxypenicillanate (660 mg., 1.88 mmoles) was stirred with 15 ml. of methylene chloride at 0°–5° C. Triethylamine (0.29 ml., 2.07 mmoles) was added, followed by alpha-toluenesulfonyl chloride (358 mg., 1.88 mmole) added over a few minutes time. The reaction was allowed to warm to room temperature. After four hours, thin layer chromatography (silica gel with 10:1 chloroform:ethyl acetate as eulant) indicated that reaction was essentially complete. The reaction mixture was extracted twice with dilute acid, twice with dilute sodium bicarbonate and once with water, dried over anhydrous sodium sulfate, filtered, and stripped to yield 745 mg. of crude product. Chromatography on 25 g. of silica gel, with methylene chloride as eluant, gave purified p-nitrobenzyl 6-beta-(alpha-toluenesulfonyloxy)penicillanate (490 mg., Rf 0.6 in above described thin layer chromatography system).

EXAMPLE 2 p-Nitrobenzyl 6-beta-(Methanesulfonyloxy)penicillanate p-Nitrobenzyl 6-beta-hydroxypenicillanate (660 mg., 1.88 mmoles) was stirred in 20 ml. of methylene chloride. Triethylamine (0.288 ml., 2.07 mmoles) and methanesulfonyl chloride (0.146 ml., 1.88 mmole) were added and the reaction stirred for 4 hours at room temperature. p-Nitrobenzyl 6-beta-(methanesulfonyloxy)-penicillanate (570 mg., Rf 0.7 on silica gel thin layer chromatography with chloroform as eluant) was isolated and purified by the methods of Example 1, substituting chloroform for methylene chloride in the column chromatography.

p-Nitrobenzyl 6-beta-(ethanesulfonyloxy)penicillanate, 6-beta-(propanesulfonyloxy)penicillanate, 6-beta-(butanesulfonyloxy)penicillanate and 6-beta-(2-methyl-1-propanesulfonyloxy)penicillanate are prepared by the same method, substituting an equivalent of the appropriate alkanesulfonyl chloride for methanesulfonyl chloride.

EXAMPLE 3 p-Nitrobenzyl 6-beta-(alpha-toluene-sulfonyloxy)penicillanate Sulfone p-Nitrobenzyl 6-beta-(alpha-toluenesulfonyloxy)-penicillanate (490 mg., 1 mmole) was dissolved in 20 ml. of methylene chloride at room temperature. m-Chloroperbenzoic acid (507 mg., 2.5 mmoles) was added and the reaction mixture stirred for approximately 16 hours at room temperature. The reaction mixture was washed twice with water, three times with dilute sodium bicarbonate, once with saturated sodium chloride, dried over anhydrous sodium sulfate, filtered and stripped to dryness to yield p-nitrobenzyl 6-beta-(alpha-toluenesulfonyloxy)penicillanate sulfone (427 mg.).

By the same method the other sulfonyloxy compounds of Example 2 are converted to the corresponding sulfones.

EXAMPLE 4

Sodium 6-beta-(alpha-Toluene-sulfonyloxy)penicillanate Sulfone

In a Paar hydrogenation apparatus, 5% Pd on CaCO$_3$ catalyst (427 mg.) in 30 ml. of 1:1 tetrahydrofuran:water was prehydrogenated under 55 psig of hydrogen for 5 minutes. p-Nitrobenzyl 6-beta-(alpha-toluenesulfonyloxy)penicillanate sulfone (427 mg.) dissolved in a mixture of 15 ml. of water and 15 ml. of tetrahydrofuran was then added and the pH was adjusted to 5.5. The mixture was then hydrogenated at 55 psig for 1 hour. The catalyst was recovered by filtration and the mother liquor stripped of tetrahydrofuran. The pH was adjusted to 7.0 and the aqueous phase extracted twice with ether. The pH was adjusted to 1.8 and the product extracted into 3 fractions of ethyl acetate. The ethyl acetate extracts were combined, dried over anhydrous sodium sulfate, filtered and stripped to yield 250 mg. of 6-beta-(alpha-toluenesulfonyloxy)penicillanic acid sulfone.

The sodium salt (250 mg.) was prepared by dissolving the free acid in tetrahydrofuran, adding an equal volume of water, adjusting the pH carefully to a constant pH of 6.8 with sodium hydroxide, stripping the tetrahydrofuran, and freeze drying the aqueous residue.

By the same method, p-nitrobenzyl 6-beta-(alphatoluenesulfonyloxy)penicillanate was converted to 6-beta-(alpha-toluenesulfonyloxy)penicillanic acid, and then to the corresponding sodium salt.

By the same method, the other sulfones of Example 3 are converted to the corresponding sulfonyloxypenicillanic acids and then to their sodium salts.

EXAMPLE 5

Sodium 6-beta-(Methanesulfonyloxy)penicillanate

By the same methods as Example 4, p-nitrobenzyl 6-beta-(methanesulfonyloxy)penicillanate (570 mg.) was converted to 6-beta-(methanesulfonyloxy)penicillanic acid (282 mg.) and then to the corresponding sodium salt (240 mg.).

EXAMPLE 6

Pivaloyloxymethyl 6-beta-(Methanesulfonyloxy)penicillanate 6-beta-Methanesulfonyloxy)penicillanate (2.95 g., 10 mmoles) is dissolved in 15 ml. of dimethylformamide. Triethylamine (1.01 g., 10 mmoles) is added with cooling and the mixture stirred for 0.5 hour at room temperature. Potassium bicarbonate (2 g., 20 mmoles) is added and stirring continued for 1 hour. Finally, chloromethyl pivalate (1.66 g., 10.8 mmoles) is added and the reaction mixture stirred for 16 hours at room temperature. The reaction mixture is poured into 250 ml. of ether, washed with multiple portions of water, then with 1N hydrochloric acid, again with water and finally brine, dried over anhydrous sodium sulfate and evaporated to dryness in vacuo to yield pivaloyloxymethyl 6-beta-(methanesulfonyloxy)penicillanate.

By the same procedure, an equivalent amount of 6-beta-(alpha-toluenesulfonyloxy)penicillanic acid is converted to pivaloyloxymethyl 6-beta-(alpha-toluenesulfonyloxy)penicillanate.

By the same procedure, employing an equivalent amount of bromomethyl acetate, 1,3-dihydro-3-oxobenzo[c]-furan-1-yl bromide or 1-ethoxycarbonyloxyethyl chloride, as appropriate, the following esters are prepared:

1-Ethoxycarbonyloxyethyl 6-beta-(alpha-toluenesulfonyloxy)penicillanate;
Acetoxymethyl 6-beta-(alpha-toluenesulfonyloxy)-penicillanate;
1-Ethoxycarbonyloxyethyl 6-beta-(methanesulfonyloxy)penicillanate;
1,3-Dihydro-3-oxobenzo[c]furan-1-yl 6-beta-(methanesulfonyloxy)penicillanate; and
Acetoxymethyl 6-beta-(ethanesulfonyloxy)penicillanate.

EXAMPLE 7

Parenteral Solutions (A) An aqueous solution is prepared which contains, per ml., the following ingredients:

| | |
|---|---|
| Penicillin G sodium | 500,000 u. |
| Sodium citrate | 13.65 mg. |
| Citric acid | 0.41 mg. |
| Sodium 6-beta-(methanesulfonyloxy)-penicillanate (amount equivalent to free acid) | 400 mg. |

The solution is subdivided into vials, 10.5 ml. per vial, and the vials freeze dried in place. Alternatively, the solution is bulk freeze dried or spray dried and the solid residue subdivided into vials so that each vial contains 5,500,000 u. of Pen G and 4.2 g. of 6-beta-(methanesulfonyl)penicillanic acid. Prior to use as a solution for intramuscular or intravenous injection, vials are reconstituted with sterile water for injection (U.S.P.) as follows:

| Volume (ml.) | Penicillin G (u./ml.) | 6-Beta-(Methane-sulfonyloxy)-penicillanic acid (mg./ml.) |
| --- | --- | --- |
| 5.25 | 1,000,000 | 800 |
| 10.5 | 500,000 | 400 |
| 21 | 250,000 | 200 |

For intravenous infusion, vials are reconstituted with isotonic sodium chloride injection (U.S.P.) or dextrose injection (U.S.P.) as follows:

| Volume (ml.) | Penicillin G (u./ml.) | 6-Beta-(Methane-sulfonyloxy)-penicillanic acid (mg./ml.) |
| --- | --- | --- |
| 21 | 250,000 | 200 |
| 26.25 | 200,000 | 160 |
| 52.5 | 100,000 | 80 |

(B) An aqueous solution is prepared which contains, per ml., the following ingredients:

| | |
| --- | --- |
| Carbenicillin disodium (amount equivalent to free acid) | 250 mg. |
| Sodium 6-beta-(alpha-toluenesulfonyloxy)-penicillanate (amount equivalent to free acid) | 250 mg. |

The mixture is subdivided into vials, 8.8 ml. per vial, and freeze dried in place. Alternatively the solution is bulk freeze dried or spray dried and the solid residue subdivided into vials so that each vial contains 1.1 g. of carbenicillin and 1.1 g. of 6-beta-(alpha-toluenesulfonyloxy)penicillanic acid. Prior to use as a solution for intramuscular or intravenous injection, vials are reconstituted with sterile water for injection (U.S.P.) as follows:

| Volume (ml.) | Penicillin G (mg./ml.) | 6-Beta-(Toluene-sulfonyloxy)-penicillanic acid (mg./ml.) |
| --- | --- | --- |
| 8.5 | 250 | 250 |
| 10.6 | 200 | 200 |
| 17.0 | 125 | 125 |

For intravenous infusion, vials are reconstituted with isotonic sodium chloride injection (U.S.P.) or dextrose injection U.S.P. as follows:

| Volume (ml.) | Carbenicillin (mg./ml.) | 6-Beta-(Toluene-sulfonyloxy)-penicillanic acid (mg./ml.) |
| --- | --- | --- |
| 17.0 | 125 | 125 |
| 21.2 | 100 | 100 |
| 28.3 | 75 | 75 |

(C) The procedure of (B) immediately above is followed, substituting 250 mg. of cephaloridine for carbenicillin to produce a suitable combination dosage form of 6-beta-(alpha-toluenesulfonyloxy)penicillanic acid and cephaloridine.

EXAMPLE 8

Parenteral Suspensions (A) Under sterile conditions, a uniform, aqueous suspension is prepared containing, per ml., the following ingredients:

| | |
| --- | --- |
| Penicillin G procaine | 200,000 u. |
| Sodium citrate | 8 mg. |
| Sodium carboxymethyl cellulose | 1.5 mg. |
| Sorbitol solution U.S.P. | 250 mg. |
| Polyvinylpyrrolidone | 0.6 mg. |
| Lecithin | 6 mg. |
| Procaine salt of 6-beta-(alpha-toluenesulfonyloxy)penicillanic acid (amount equivalent to free acid | 100 mg. |

The homogeneous suspension is filled into 10 ml. vials and is suitable for intramuscular injection.

(B) A sterile, homogeneous blend of the following, finely divided ingredients is prepared:

| | |
| --- | --- |
| Ampicillin trihydrate (amount equivalent to free acid) | 1000 g. |
| Procaine | 500 g. |
| 6-beta-(Methanesulfonyloxy)penicillanic acid | 1000 g. |

The blend is filled into vials so as to contain 11 g. of ampicillin, 0.55 g. of procaine and 1.1 g. of 6-beta-(methanesulfonyloxy)penicillanic acid. Prior to intramuscular injection the contents are suspended in sterile water for injection (U.S.P.) as follows:

| Volume (ml.) | Ampicillin (mg./ml.) | 6-Beta-(Methane-sulfonyloxy)-penicillanic Acid (mg./ml.) |
| --- | --- | --- |
| 10.5 | 100 | 100 |
| 15.75 | 75 | 75 |
| 21 | 50 | 50 |

EXAMPLE 9

Capsules

Capsules are prepared by blending the following ingredients in the proportion by weight indicated:

| | |
| --- | --- |
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 | and adding sufficient ampicillin trihydrate and pivaloyloxy-methyl 6-beta-(methanesulfonyloxy)penicillanate to provide capsules containing the following weights (equivalent to non-hydrated or non-esterified forms) of the active ingredients per capsule:

| Ampicillin Trihydrate | Pivaloyloxymethyl 6-beta(Methanesulfonyloxy)-penicillanate |
| --- | --- |
| 125 mg. | 125 mg. |
| 250 mg. | 125 mg. |
| 250 mg. | 250 mg. |
| 250 mg. | 375 mg. |
| 500 mg. | 500 mg. |

The compositions are filled into conventional hard gelatin capsules of suitable size.

To prepare other combination capsules, other beta-lactam antibiotics (e.g. cephradine, cefazoline sodium) are substituted for ampicillin trihydrate in like quantities.

EXAMPLE 10

Tablets

A tablet base is prepared by blending the following ingredients in the proportion by weight indicated:
Sucrose, U.S.P. : 80.3
Tapioca Starch : 13.2
Magnesium Stearate : 6.5

Into this tablet base is blended sufficient pivaloyloxymethyl 6-beta-(alpha-toluenesulfonyloxy)-penicillanate and penicillin G potassium to provide tablets containing the following quantities (equivalent to non-salt or non-esterified forms) of active ingredients:

| Penicillin V potassium | 6-beta-(alpha-Toluene sulfonyloxy)penicillanate |
| --- | --- |
| 125 mg. | 250 mg. |
| 200 mg. | 400 mg. |
| 250 mg. | 125 mg. |
| 250 mg. | 250 mg. |

Appropriate quantities of the various blends are compressed into tablets of the desired potency.

PREPARATION 1 p-Nitrobenzyl 6-alpha-Hydroxypenicillanate 6-alpha-Hydroxypenicillanate (26.0 g., 0.12 mole) was stirred in 450 ml. of dimethylformamide. Triethylamine (16.8 ml., 0.12 mole) and sodium bicarbonate (1.51 g., 0.018 mole) were added followed by p-nitrobenzyl bromide (27.2 g., 0.126 mole). The reaction mixture was stirred overnight at room temperature. The solvent was evaporated in vacuo. The residue was taken up in ethyl acetate, the ethyl acetate washed twice with dilute hydrochloric acid, twice with saturated sodium bicarbonate, once with water, dried over anhydrous sodium sulfate, filtered and evaporated to dryness in vacuo (24 g.). Recrystallization from chloroform/hexane gave purified p-nitrobenzyl 6-alpha-hydroxypenicillanate (12.4 g.) in two crops.

PREPARATION 2 p-Nitrobenzyl 6-Ketopenicillanate p-Nitrobenzyl 6-alpha-hydroxypenicillante (4.58 g., 13 mmoles) was dissolved in 40 ml. of dimethylsulfoxide. Pyridine (1.05 ml., 13 mmoles) and then trifluoroacetic acid (0.50 ml., 6.5 mmoles) were added, followed by diisopropyl carbodimide (6.08 ml., 39 mmoles). The reaction mixture was stirred for 2 hours. Excess carbodiimide was decomposed by the slow addition of oxalic acid (3.25 g., 26 mmoles) in 25 ml. of dimethylsulfoxide.

The mixture was then added to 700 ml. of ice and water, and insolubles removed by filtration with water and benzene wash. The combined filtrate and washes were extracted with benzene (4 portions). The combined benzene extracts were back-washed with water and then saturated sodium chloride, dried over anhydrous sodium sulfate and evaporated to dryness to yield p-nitrobenzyl 6-ketopenicillanate, contaminated with urea, assumed to contain the theoretical yield of product (4.55 g.).

PREPARATION 3 p-Nitrobenzyl 6-beta-Hydroxypenicillanate

Crude p-nitrobenzyl 6-ketopenicillanate (from Preparation 2, assumed to contain 4.55 g., 13 mmoles) was dissolved in 100 ml. of tetrahydrofuran and stirred at −15° C. Zinc borohydride in ether (90 ml. containing 13 mmoles) was added. The reaction was warmed to 0° C. and stirred for 10 minutes. Water (50 ml.) was added slowly. The pH was adjusted from 7.3 to 6.8 with hydrochloric acid. The organic solvents were removed by evaporation in vacuo. The aqueous residue was adjusted to pH 2.0 and product extracted into methylene chloride in 3 portions. The methylene chloride was back washed with 5% potassium bicarbonate and then water, dried over anhydrous sodium sulfate, filtered and evaporated to dryness (4 g.). The crude was chromatographed on 50 g. of silica gel with chloroform as eluant. Clean middle fractions were combined and evaporated to dryness to yield purified p-nitrobenzyl 6-beta-hydroxypenicillanate (1.75 g., tlc: R$_f$0.25 on silica gel with chloroform/ethyl acetate 10/1 as eluant).

I claim:

1. A method of treating bacterial infections in a mammal which comprises administering to said mammal an effective synergistic mixture of a beta-lactam antibiotic selected from the group consisting of penicillin G sodium, penicillin G potassium, penicillin G procaine, penicillin V, ampicillin sodium, ampicillin trihydrate, amoxicillin, carbenicillin disodium, cefachlor, cefaperazone sodium, cephradine cephaloridine, cefazolin sodium, cephalothin sodium, and cephalexin monohydrate, in the amount of 1–4 g./day in single or divided doses, together with a compound of the formula

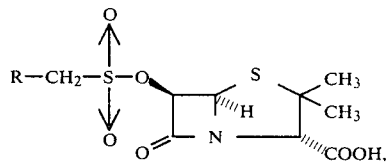

a pharmaceutically acceptable salt thereof, or a pivaloyloxymethyl, acetoxymethyl, 1,3-dihydro-3-oxo-benzo[c]furan-1-yl or 1-ethoxycarbonyloxyethyl ester thereof, wherein R is hydrogen or phenyl, in an amount substantially equal by weight to said beta-lactam antibiotic.

2. A method of claim 1 wherein the bacterial infection is a Proteus infection.

3. A method of claim 2 wherein R is hydrogen.

4. A method of claim 3 wherein the beta-lactam antibiotic is penicillin G sodium, penicillin G potassium or penicillin G procaine.

5. A method of claim 3 wherein the beta-lactam antibiotic is ampicillin sodium or ampicillin trihydrate.

6. A method of claim 3 wherein the beta-lactam antibiotic is carbenicillin disodium.

7. A method of claim 3 wherein the beta-lactam is cephaloridine, cefazolin sodium or cephalothin sodium.

8. A method of claim 2 wherein R is phenyl.

9. A method of claim 8 wherein the beta-lactam antibiotic is penicillin G sodium, penicillin G potassium or penicillin G procaine.

10. A method of claim 8 wherein the beta-lactam antibiotic is ampicillin sodium or ampicillin trihydrate.

11. A method of claim 8 wherein the beta-lactam antibiotic is carbenicillin disodium.

12. A method of claim 8 wherein the beta-lactam antibiotic is cephaloridine, cefazolin sodium or cephalothin sodium.

13. A pharmaceutical composition suitable for oral or parenteral administration as an antibacterial in a mammal which comprises an effective synergistic mixture of a beta-lactam antibiotic selected from the group consisting of penicillin G sodium, penicillin G potassium, penicillin G procaine, penicillin V, ampicillin sodium, ampicillin trihydrate, carbenicillin disodium, cefachlor, cefaperazone sodium, cephradine, cephaloridine, cefazolin sodium, cephalothin sodium, and cephalexin monohydrate together with a compound of the formula

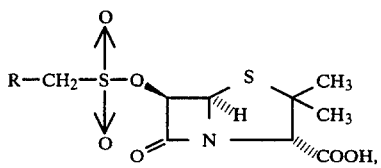

a pharmaceutically acceptable salt thereof, or a pivaloyloxymethyl, acetoxymethyl, 1,3-dihydro-3-oxobenzo[c]furan-1-yl or 1-ethoxycarbonyloxyethyl ester thereof, wherein R is hydrogen or phenyl, in an amount substantially equal by weight of said beta-lactam antibiotic, and a pharmaceutically acceptable carrier, the amount of the combination of active ingredients in the carrier being suitable for the daily dosage of 1 to 4 g. of the beta-lactam antibiotic and a substantially equal weight of one of said compounds in single or divided doses.

14. A pharmaceutical composition of claim 13 wherein R is hydrogen.

15. A pharmaceutical composition of claim 14 wherein the beta-lactam antibiotic is penicillin G sodium, penicillin G potassium or penicillin G procaine.

16. A pharmaceutical composition of claim 14 wherein the beta-lactam antibiotic is ampicillin sodium or ampicillin trihydrate.

17. A pharmaceutical composition of claim 14 wherein the beta-lactam antibiotic is carbenicillin disodium.

18. A pharmaceutical composition of claim 14 wherein the beta-lactam antibiotic is cephaloridine, cefazolin sodium or cephalothin sodium.

19. A pharmaceutical composition of claim 13 wherein R is phenyl.

20. A pharmaceutical composition of claim 19 wherein the beta-lactam antibiotic is penicillin G sodium, penicillin G potassium or penicillin G procaine.

21. A pharmaceutical composition of claim 19 wherein the beta-lactam antibiotic is ampicillin sodium or ampicillin trihydrate.

22. A pharmaceutical composition of claim 19 wherein the beta-lactam antibiotic is carbenicillin disodium.

23. A pharmaceutical composition of claim 19 wherein the beta-lactam antibiotic is cephaloridine, cefazolin sodium or cephalothin sodium.

24. A method of treating bacterial infections in a mammal which comprises administering to said mammal ampicillin, in the amount of 1 to 4 g/day in single or divided doses, together with a compound of the formula

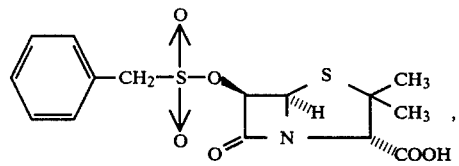

a pharmaceutically acceptable salt thereof, or a pivaloyloxymethyl, acetoxymethyl, 1,3-dihydro-3-oxobenzo[c]furan-1-yl or 1-ethoxycarbonyloxyethyl ester thereof in an amount substantially equal by weight to said ampicillin.

25. A pharmaceutical composition suitable for oral or parenteral administration as an antibacterial in a mammal which comprises ampicillin together with a compound of the formula

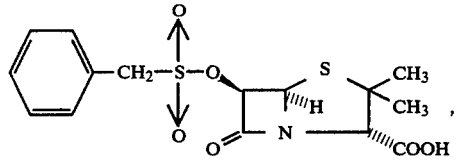

a pharmaceutically acceptable salt thereof or a pivaloyloxymethyl, acetoxymethyl, 1,3-dihydro-3-oxo-benzo[c]furan-1-yl or 1-ethoxycarbonyloxyethyl ester thereof in an amount substantially equal by weight of said ampicillin and a pharmaceutically acceptable carrier, the amount of the combination of active ingredients in the carrier being suitable for the daily dosage of 1 to 4 g. of said ampicillin and a substantially equal weight of one of said compounds in single or divided doses.

26. An antibacterial pharmaceutical composition comprising ampicillin and

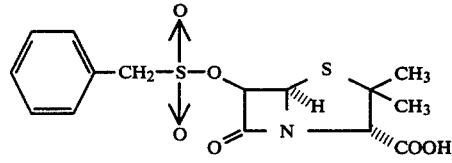

in a ratio of 1:1.

* * * * *